(12) United States Patent
Cully et al.

(10) Patent No.: US 11,911,537 B2
(45) Date of Patent: Feb. 27, 2024

(54) LENGTH EXTENSIBLE IMPLANTABLE DEVICE AND METHODS FOR MAKING SUCH DEVICES

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/953,662

(22) Filed: Nov. 20, 2020

(65) Prior Publication Data

US 2021/0138121 A1    May 13, 2021

Related U.S. Application Data

(62) Division of application No. 14/558,296, filed on Dec. 2, 2014, now Pat. No. 10,842,918.

(60) Provisional application No. 61/912,414, filed on Dec. 5, 2013.

(51) Int. Cl.
| | |
|---|---|
| *A61F 2/06* | (2013.01) |
| *A61F 2/07* | (2013.01) |
| *A61F 2/82* | (2013.01) |
| *A61L 31/14* | (2006.01) |
| *B29D 23/00* | (2006.01) |

(Continued)

(52) U.S. Cl.
CPC ............ *A61L 31/146* (2013.01); *A61F 2/06* (2013.01); *A61F 2/07* (2013.01); *A61F 2/82* (2013.01); *B29D 23/001* (2013.01); *B32B 37/12* (2013.01); *B32B 37/142* (2013.01); *B32B 38/0012* (2013.01); *A61F 2210/0057* (2013.01); *A61F 2210/0071* (2013.01); *A61F 2210/0076* (2013.01); *A61F 2220/005* (2013.01); *A61F 2240/001* (2013.01); *A61F 2250/0028* (2013.01); *A61F 2250/0037* (2013.01);

(Continued)

(58) Field of Classification Search
CPC ............................................... A61F 2250/0071
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |

(Continued)

FOREIGN PATENT DOCUMENTS

| | | |
|---|---|---|
| CA | 2462509 A1 | 4/2003 |
| CN | 101420913 A | 4/2009 |

(Continued)

OTHER PUBLICATIONS

European Search Report and Search Opinion Received for EP Application No. 16899644.5, dated Oct. 30, 2019, 8 pages.

(Continued)

*Primary Examiner* — Jacqueline Woznicki (57) ABSTRACT

A length extensible implantable device includes a porous member and a longitudinal constraining member. The longitudinal constraining member can constrain at least a portion, up to the entire length of, the porous member in the longitudinal direction. The length of the longitudinally constrained portion can be expanded by applying force to the porous member. The porous member may be a porous tubular member.

19 Claims, 4 Drawing Sheets

(51) Int. Cl.
*B32B 37/12* (2006.01)
*B32B 37/14* (2006.01)
*B32B 38/00* (2006.01)
*B29K 27/18* (2006.01)

(52) U.S. Cl.
CPC ............... *A61F 2250/0048* (2013.01); *A61F 2250/0071* (2013.01); *B29K 2027/18* (2013.01)

(56) References Cited

U.S. PATENT DOCUMENTS

| | | | |
|---|---|---|---|
| 4,332,035 | A | 6/1982 | Mano |
| 4,877,661 | A | 10/1989 | House et al. |
| 4,955,899 | A | 9/1990 | Della et al. |
| 5,026,513 | A | 6/1991 | House et al. |
| 5,064,435 | A | 11/1991 | Porter |
| 5,071,609 | A | 12/1991 | Tu et al. |
| 5,476,589 | A | 12/1995 | Bacino |
| 5,534,007 | A | 7/1996 | St et al. |
| 5,549,663 | A | 8/1996 | Cottone, Jr. |
| 5,673,102 | A | 9/1997 | Suzuki et al. |
| 5,708,044 | A | 1/1998 | Branca |
| 5,718,973 | A | 2/1998 | Lewis et al. |
| 5,749,852 | A | 5/1998 | Schwab et al. |
| 5,752,934 | A | 5/1998 | Campbell et al. |
| 5,759,192 | A | 6/1998 | Saunders |
| 5,769,884 | A | 6/1998 | Solovay |
| 5,772,884 | A | 6/1998 | Tanaka et al. |
| 5,788,626 | A | 8/1998 | Thompson |
| 5,814,405 | A | 9/1998 | Branca et al. |
| 5,824,043 | A | 10/1998 | Cottone, Jr. |
| 5,843,158 | A | 12/1998 | Lenker et al. |
| 5,843,161 | A | 12/1998 | Solovay |
| 5,843,171 | A * | 12/1998 | Campbell ........ A61B 17/12109 606/198 |
| 5,853,419 | A | 12/1998 | Imran |
| 5,925,061 | A | 7/1999 | Ogi et al. |
| 5,935,162 | A | 8/1999 | Dang |
| 5,957,974 | A | 9/1999 | Thompson et al. |
| 6,010,529 | A | 1/2000 | Herweck et al. |
| 6,013,854 | A | 1/2000 | Moriuchi |
| 6,042,588 | A | 3/2000 | Munsinger et al. |
| 6,042,605 | A | 3/2000 | Martin et al. |
| 6,042,606 | A | 3/2000 | Frantzen |
| 6,110,198 | A | 8/2000 | Fogarty et al. |
| 6,156,064 | A | 12/2000 | Chouinard |
| 6,161,399 | A | 12/2000 | Jayaraman |
| 6,165,211 | A | 12/2000 | Thompson |
| 6,174,329 | B1 | 1/2001 | Callol et al. |
| 6,190,406 | B1 | 2/2001 | Duerig et al. |
| 6,217,609 | B1 | 4/2001 | Haverkost |
| 6,245,012 | B1 | 6/2001 | Kleshinski |
| 6,261,320 | B1 | 7/2001 | Tam et al. |
| 6,261,620 | B1 | 7/2001 | Leadbeater |
| 6,315,791 | B1 | 11/2001 | Gingras et al. |
| 6,336,937 | B1 | 1/2002 | Vonesh et al. |
| 6,352,552 | B1 | 3/2002 | Levinson et al. |
| 6,379,382 | B1 | 4/2002 | Yang |
| 6,436,132 | B1 | 8/2002 | Patel et al. |
| 6,461,665 | B1 | 10/2002 | Scholander |
| 6,488,701 | B1 | 12/2002 | Nolting et al. |
| 6,541,589 | B1 | 4/2003 | Baillie |
| 6,620,190 | B1 | 9/2003 | Colone |
| 6,626,939 | B1 | 9/2003 | Burnside et al. |
| 6,673,102 | B1 | 1/2004 | Vonesh et al. |
| 6,673,107 | B1 | 1/2004 | Brandt et al. |
| 6,730,120 | B2 | 5/2004 | Berg et al. |
| 6,755,856 | B2 | 6/2004 | Fierens et al. |
| 6,758,858 | B2 | 7/2004 | McCrea et al. |
| 6,890,350 | B1 | 5/2005 | Walak |
| 7,022,132 | B2 * | 4/2006 | Kocur .................... A61F 2/915 623/1.11 |
| 7,049,380 | B1 | 5/2006 | Chang et al. |
| 7,083,642 | B2 | 8/2006 | Sirhan et al. |
| 7,105,018 | B1 | 9/2006 | Yip et al. |
| 7,306,729 | B2 | 12/2007 | Bacino et al. |
| 7,419,678 | B2 | 9/2008 | Falotico |
| 7,462,675 | B2 | 12/2008 | Chang et al. |
| 7,531,611 | B2 | 5/2009 | Sabol et al. |
| 7,704,274 | B2 | 4/2010 | Boyle et al. |
| 7,789,908 | B2 | 9/2010 | Sowinski et al. |
| 7,811,314 | B2 | 10/2010 | Fierens et al. |
| 7,815,763 | B2 | 10/2010 | Fierens et al. |
| 7,887,562 | B2 | 2/2011 | Young et al. |
| 7,927,364 | B2 | 4/2011 | Fierens et al. |
| 7,927,365 | B2 | 4/2011 | Fierens et al. |
| 7,935,141 | B2 | 5/2011 | Randall et al. |
| 7,967,829 | B2 | 6/2011 | Gunderson et al. |
| 8,048,440 | B2 | 11/2011 | Chang et al. |
| 8,545,525 | B2 | 10/2013 | Surti et al. |
| 8,585,753 | B2 | 11/2013 | Scanlon et al. |
| 8,728,103 | B2 | 5/2014 | Surti et al. |
| 8,801,774 | B2 | 8/2014 | Silverman |
| 8,936,634 | B2 | 1/2015 | Irwin et al. |
| 9,241,695 | B2 | 1/2016 | Peavey et al. |
| 9,345,601 | B2 | 5/2016 | Jantzen et al. |
| 9,399,085 | B2 | 7/2016 | Cleek et al. |
| 9,554,786 | B2 | 1/2017 | Carley et al. |
| 9,681,948 | B2 | 6/2017 | Levi et al. |
| 9,737,422 | B2 | 8/2017 | Armstrong et al. |
| 9,795,496 | B2 | 10/2017 | Armstrong et al. |
| 9,833,343 | B2 | 12/2017 | Burnside et al. |
| 9,839,540 | B2 | 12/2017 | Armstrong et al. |
| 9,931,193 | B2 | 4/2018 | Cully et al. |
| 10,166,128 | B2 | 1/2019 | Armstrong et al. |
| 10,279,084 | B2 | 5/2019 | Goepfrich et al. |
| 10,335,298 | B2 | 7/2019 | Armstrong et al. |
| 10,507,124 | B2 | 12/2019 | Armstrong et al. |
| 11,116,621 | B2 | 9/2021 | Cully et al. |
| 11,357,611 | B2 | 6/2022 | Cully et al. |
| 2001/0053929 | A1 | 12/2001 | Vonesh et al. |
| 2002/0038140 | A1 | 3/2002 | Yang et al. |
| 2002/0076542 | A1 | 6/2002 | Kramer et al. |
| 2002/0161388 | A1 | 10/2002 | Samuels et al. |
| 2002/0198588 | A1 | 12/2002 | Armstrong et al. |
| 2003/0055494 | A1 | 3/2003 | Bezuidenhout et al. |
| 2003/0060871 | A1 | 3/2003 | Hill et al. |
| 2003/0180488 | A1 | 9/2003 | Lim et al. |
| 2004/0024442 | A1 | 2/2004 | Sowinski et al. |
| 2004/0024448 | A1 | 2/2004 | Chang et al. |
| 2004/0044400 | A1 | 3/2004 | Cheng et al. |
| 2004/0044401 | A1 | 3/2004 | Bales et al. |
| 2004/0093065 | A1 | 5/2004 | Yachia et al. |
| 2004/0133266 | A1 | 7/2004 | Clerc et al. |
| 2004/0162606 | A1 | 8/2004 | Thompson |
| 2004/0170782 | A1 | 9/2004 | Wang et al. |
| 2004/0224442 | A1 | 11/2004 | Grigg |
| 2004/0260277 | A1 | 12/2004 | Maguire |
| 2005/0080476 | A1 | 4/2005 | Gunderson et al. |
| 2005/0137680 | A1 | 6/2005 | Ortiz et al. |
| 2005/0273149 | A1 | 12/2005 | Tran et al. |
| 2005/0283224 | A1 | 12/2005 | King |
| 2006/0009835 | A1 | 1/2006 | Osborne et al. |
| 2006/0015171 | A1 | 1/2006 | Armstrong |
| 2006/0036311 | A1 | 2/2006 | Nakayama et al. |
| 2006/0106337 | A1 | 5/2006 | Blankenship |
| 2006/0118236 | A1 | 6/2006 | House et al. |
| 2006/0135985 | A1 | 6/2006 | Cox et al. |
| 2006/0161241 | A1 | 7/2006 | Barbut et al. |
| 2006/0190070 | A1 | 8/2006 | Dieck et al. |
| 2006/0259133 | A1 | 11/2006 | Sowinski et al. |
| 2006/0271091 | A1 | 11/2006 | Campbell et al. |
| 2006/0276883 | A1 | 12/2006 | Greenberg et al. |
| 2007/0012624 | A1 | 1/2007 | Bacino et al. |
| 2007/0060999 | A1 | 3/2007 | Randall et al. |
| 2007/0088421 | A1 | 4/2007 | Loewen |
| 2007/0129786 | A1 | 6/2007 | Beach et al. |
| 2007/0207186 | A1 | 9/2007 | Scanlon et al. |
| 2007/0207816 | A1 | 9/2007 | Spain |
| 2007/0208421 | A1 | 9/2007 | Quigley |
| 2007/0213800 | A1 | 9/2007 | Fierens et al. |
| 2007/0250146 | A1 | 10/2007 | Cully et al. |
| 2007/0250153 | A1 | 10/2007 | Cully et al. |
| 2007/0254012 | A1 | 11/2007 | Ludwig et al. |

(56) References Cited

U.S. PATENT DOCUMENTS

| | | |
|---|---|---|
| 2008/0051876 A1 | 2/2008 | Ta et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0182413 A1 | 7/2009 | Burkart et al. |
| 2009/0264989 A1 | 10/2009 | Bonhoeffer et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0211166 A1* | 8/2010 | Miller ............... A61F 2/2448 623/2.37 |
| 2010/0256738 A1 | 10/2010 | Berglund |
| 2010/0286760 A1 | 11/2010 | Beach et al. |
| 2010/0305682 A1 | 12/2010 | Furst |
| 2011/0009953 A1 | 1/2011 | Luk et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0245745 A1 | 9/2013 | Vong et al. |
| 2013/0253466 A1 | 9/2013 | Campbell et al. |
| 2013/0297003 A1 | 11/2013 | Pinchuk |
| 2014/0121746 A1* | 5/2014 | Kusleika ............. A61F 2/07 623/1.11 |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0005870 A1 | 1/2015 | Kovach et al. |
| 2015/0157770 A1 | 6/2015 | Cully et al. |
| 2015/0313871 A1 | 11/2015 | Li et al. |
| 2016/0015422 A1 | 1/2016 | De et al. |
| 2016/0184079 A1 | 6/2016 | Scutti et al. |
| 2017/0065400 A1 | 3/2017 | Armstrong et al. |
| 2017/0105854 A1 | 4/2017 | Treacy et al. |
| 2017/0106176 A1 | 4/2017 | Taft et al. |
| 2017/0216062 A1 | 8/2017 | Armstrong et al. |
| 2018/0177583 A1 | 6/2018 | Cully et al. |
| 2019/0125517 A1 | 5/2019 | Cully et al. |
| 2019/0209739 A1 | 7/2019 | Goepfrich et al. |
| 2019/0216592 A1 | 7/2019 | Cully et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2021/0038413 A1 | 2/2021 | Cully et al. |
| 2021/0068996 A1 | 3/2021 | Armstrong et al. |
| 2021/0077246 A1 | 3/2021 | Cully et al. |
| 2021/0236139 A1* | 8/2021 | Connor ............. A61B 17/1214 |

FOREIGN PATENT DOCUMENTS

| | | |
|---|---|---|
| CN | 101926699 A | 12/2010 |
| CN | 201744060 U | 2/2011 |
| CN | 102015009 A | 4/2011 |
| CN | 103945796 A | 7/2014 |
| CN | 105025848 A | 11/2015 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1666003 A1 | 6/2006 |
| EP | 1946721 A1 | 7/2008 |
| EP | 2255750 A2 | 12/2010 |
| JP | 02-000645 A | 1/1990 |
| JP | 09-241412 A | 9/1997 |
| JP | 11-197252 A | 7/1999 |
| JP | 11-290448 A | 10/1999 |
| JP | 11-512635 A | 11/1999 |
| JP | 2001-509702 A | 7/2001 |
| JP | 2002-531219 A | 9/2002 |
| JP | 2007-526098 A | 9/2007 |
| JP | 2008-506459 A | 3/2008 |
| JP | 2008-173461 A | 7/2008 |
| JP | 2010-500107 A | 1/2010 |
| JP | 2010-504174 A | 2/2010 |
| JP | 2010-535075 A | 11/2010 |
| JP | 2015-502205 A | 1/2015 |
| JP | 2015-513931 A | 5/2015 |
| JP | 2018-134425 A | 8/2018 |
| JP | 2019-048083 A | 3/2019 |
| JP | 2019-514493 A | 6/2019 |
| JP | 2021-122433 A | 8/2021 |
| JP | 2021-168971 A | 10/2021 |
| NO | 94/16802 A1 | 8/1994 |
| RU | 2124986 C1 | 1/1999 |
| WO | 94/13224 A1 | 6/1994 |
| WO | 95/05555 A1 | 2/1995 |
| WO | 95/09586 A1 | 4/1995 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/41649 A1 | 7/2000 |
| WO | 00/47271 A1 | 8/2000 |
| WO | 01/64278 A1 | 9/2001 |
| WO | 01/74272 A2 | 10/2001 |
| WO | 02/60506 A1 | 8/2002 |
| WO | 03/03946 A1 | 1/2003 |
| WO | 03/20175 A1 | 3/2003 |
| WO | 2004/000375 A1 | 12/2003 |
| WO | 2006/019626 A2 | 2/2006 |
| WO | 2006/058322 A2 | 6/2006 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/021006 A3 | 8/2008 |
| WO | 2008/097589 A1 | 8/2008 |
| WO | 2009/017827 A1 | 2/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/132707 A1 | 11/2010 |
| WO | 2010/150208 A2 | 12/2010 |
| WO | 2011/098565 A1 | 8/2011 |
| WO | 2012/011261 A1 | 1/2012 |
| WO | 2012/099979 A1 | 7/2012 |
| WO | 2012/158944 A1 | 11/2012 |
| WO | 2013/074663 A2 | 5/2013 |
| WO | 2013/074990 A1 | 5/2013 |
| WO | 2013/109337 A1 | 7/2013 |
| WO | 2013/138789 A1 | 9/2013 |
| WO | 2017/038145 A1 | 3/2017 |
| WO | 2017/184153 A1 | 10/2017 |
| WO | 2019/074869 A1 | 4/2019 |

OTHER PUBLICATIONS

European Search Report and Search Opinion Received for EP Application No. 18167101, dated Jul. 25, 2018, 9 pages.

European Search Report from EP16196687.4, dated Nov. 21, 2017, 5 pages.

Extended European Search Report issued in EP Application No. 17186750.0, dated Oct. 24, 2017, 7 pages.

(56) References Cited

OTHER PUBLICATIONS

International Preliminary Report on Patentability issued in PCT/US2016/028671, dated Nov. 1, 2018, 12 pages.
International Preliminary Report on Patentability received for PCT Patent Application No. PCT/US11/61165, dated Jul. 25, 2013, 14 pages.
International Preliminary Report on Patentability received for PCT Patent Application No. PCT/US12/65066, dated May 30, 2014, 14 pages.
International Preliminary Report on Patentability received for PCT Patent Application No. PCT/US14/68430, dated Jun. 16, 2016, 8 pages.
International Preliminary Report on Patentability received for PCT Patent Application No. PCT/US2013/076405, dated Jul. 2, 2015, 10 pages.
International Preliminary Report on Patentability received for PCT Patent Application No. PCT/US2014/013496, dated Aug. 11, 2016, 7 pages.
International Search Report and Written Opinion for Application No. PCT/US2016/028671 dated Jul. 28, 2016.
International Search Report and Written Opinion for Application No. PCT/US2016/028671, dated Jul. 28, 2016, 19 pages.
International Search Report and Written Opinion for PCT/US2012/064908 dated Feb. 4, 2013, corresponding to U.S. Appl. No. 13/675,730, 11 pages.
International Search Report and Written Opinion for PCT/US2012/066518, dated Feb. 4, 2013, corresponding to U.S. Appl. No. 13/351,052, 12 pages.
International Search Report and Written Opinion for PCT/US2014/068430 dated Feb. 20, 2015, corresponding to U.S. Appl. No. 14/558,296, 9 pages.
International Search Report and Written Opinion issued in PCT/US2011/061165, dated Oct. 1, 2012, 20 pages.
International Search Report and Written Opinion issued in PCT/US2012/066518, dated Feb. 4, 2013, 10 pages.
International Search Report and Written Opinion issued in PCT/U.S. Pat. No. 2012065066, dated Nov. 11, 2013, 9 pages.
International Search Report for PCT/US2013/076405 dated May 6, 2014, corresponding to U.S. Appl. No. 14/132,767, 8 pages.
International Search Report for PCT/US2014/013496 dated Dec. 2, 2014, corresponding to U.S. Appl. No. 13/755,481, 4 pages.
International Search Report issued in PCT/US2013/076405, dated May 6, 2014, 7 pages.
International Search Report issued in PCT/US2014/013496, dated Dec. 2, 2014, 3 pages.
International Written Opinion received for PCT Patent Application No. PCT/US2014/013496, dated Dec. 2, 2014, 5 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.
Partial International Search Report for PCT/US2012/065066, dated Jul. 1, 2013, corresponding to U.S. Appl. No. 13/675,959, 3 pages.
Bent definition and meaning, Collins English Dictionary,https://www.collinsdictionary.com/us/dictionary/english/bent, accessed May 27, 2022 (Year: 2022).

\* cited by examiner

LENGTH EXTENSIBLE IMPLANTABLE DEVICE AND METHODS FOR MAKING SUCH DEVICES

CROSS-REFERENCE TO RELATED APPLICATION

This application is a divisional of U.S. patent application Ser. No. 14/558,296, filed Dec. 2, 2014, now U.S. Pat. No. 10,842,918, issued Nov. 24, 2020, which claims the benefit of U.S. Provisional Application 61/912,414, filed Dec. 5, 2013, both of which are incorporated herein by reference in their entireties for all purposes.

TECHNICAL FIELD

This disclosure relates to length extensible implantable devices and methods for making such devices that may be used for providing a lumen for fluid flow in bodily cavities, organs, and vessels within a patient.

BACKGROUND

Medical devices are frequently used to treat the anatomy of patients. Such devices can be permanently or semi-permanently implanted in the anatomy to provide treatment to a patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site using a catheter.

Implantable devices such as grafts and stent-grafts are used in a variety of places in the human body to repair, support, and/or replace anatomical lumens, such as blood vessels, respiratory ducts, gastrointestinal ducts, and the like. Such devices can, for example, provide lumens for blood flow. In such configurations, flexible and durable devices are needed.

The selection of such implantable devices can pose potential issues. For example, the particularities of the anatomy of one patient may require a device having a different length than a device suitable for another patient. As a result, it may be difficult to determine the necessary size of a device, and, in many instances, the desired device size may be difficult to obtain.

As such, there is an ongoing need to provide devices, such as grafts and/or stent-grafts, which have adjustable length properties to provide a range of available lengths. Such devices may improve the ability of a treatment provider to properly size a device for the anatomy of a patient.

SUMMARY

In a first general aspect, a length extensible implantable device for supporting, repairing, and/or replacing a lumen in the body of a patient includes a porous tubular member capable of being extended to a desired length. The porous tubular member comprises a longitudinally compressed portion covered and maintained in the compressed configuration by a longitudinal constraining member. The longitudinal constraining member can comprise a film wrap or a perforated tube, among other structures.

In various implementations, a length extensible implantable device is formed by longitudinally compressing a porous tubular member, surrounding a portion of the tubular member with a longitudinal constraining member, and releasing the compressive force. In such implementations, the longitudinally constraining member constrains the portion of the tubular member in the longitudinally compressed configuration. The longitudinal constraining member can optionally be secured to the portion of the porous tubular member by, for example, an adhesive. More than one longitudinal constraining member can used. Further, more than one portion of the porous tubular member can be surrounded by one or more longitudinal constraining members.

The details of one or more embodiments are set forth in the accompanying drawings and the description below. Other features, objects, and advantages will be apparent from the description and the drawings, and from the claims.

BRIEF DESCRIPTION OF THE DRAWINGS

Like reference symbols in the various drawings indicate like elements.

DETAILED DESCRIPTION OF THE DRAWINGS

This disclosure describes devices, systems, and methods that are useful, for example, for repairing, supporting, and/or replacing anatomical lumens. Several implantable medical devices are described herein, and in general any of the features described with respect to a particular device may also be used with any of the other devices described herein. In some examples, one or more features described with respect to a particular device may be added to or included with another device. Also, various combinations or sub-combinations of any of the features described herein may generally be used with any of the devices described herein.

In general, any of the implantable devices described herein can be delivered to, and deployed at, an in vivo deployment site within a body of a patient using variously minimally invasive surgical techniques. Likewise, these devices may also be surgically implanted via vascular surgical techniques.

Further, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter, and the device and delivery catheter may be loaded into a delivery sheath. The delivery sheath may be introduced to the vasculature of the patient and advanced through the vasculature, until a distal end of the delivery sheath is located at or near the target in vivo deployment site. The implantable medical device may be deployed at the deployment site, for example, by retracting the delivery sheath and/or advancing the delivery catheter and the implantable medical device and detaching the implantable medical device from the delivery catheter. The delivery catheter and delivery sheath can then be withdrawn or retracted from the body of the patient.

Any of the implantable medical devices discussed herein can be used to repair, replace, and/or provide support to a body lumen. In various embodiments, implantable medical devices of the present disclosure can be used in a body lumen, including those within the circulatory and gastrointestinal systems.

As used herein, "implantable" means implanted in the body of a patient for more than 29 days.

As used herein, the term "constrain" means: (i) to limit extension, occurring either through self-expansion or assisted expansion, of the length of an implantable device; or (ii) to cover or surround, but not otherwise restrain, an implantable device such as for storage or biocompatibility reasons and/or to provide protection to the implantable device and/or the vasculature.

Figure 1A:
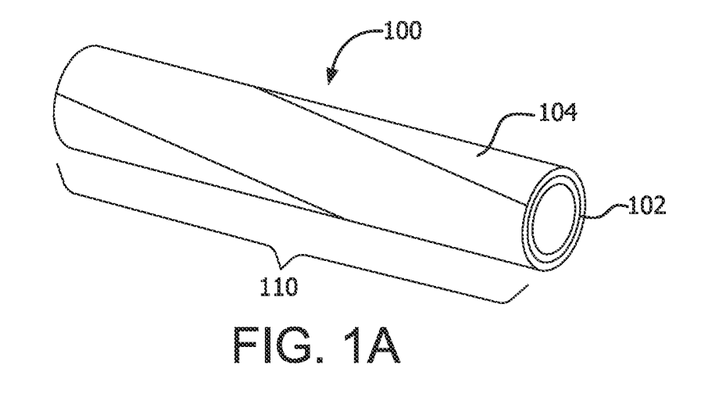
FIGS. 1A-1C are perspective views of various length extensible implantable devices in accordance with the present disclosure.
Figure 1B:
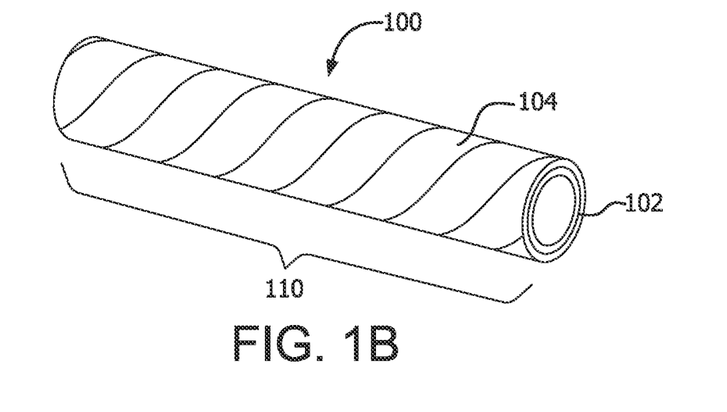
Figure 1C:
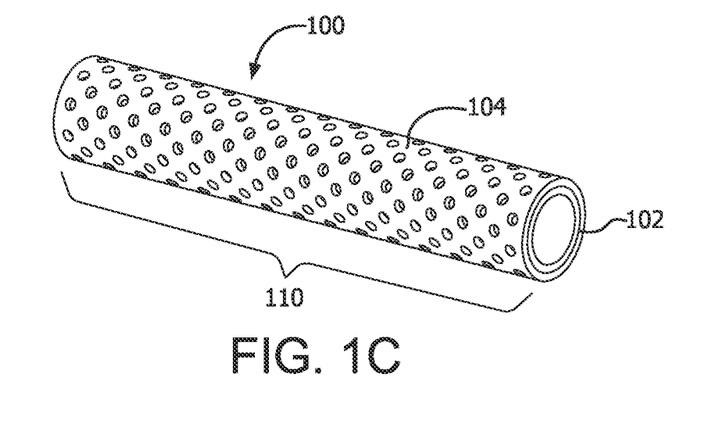

FIGS. 1A-1C describe perspective views of various example length extensible implantable devices 100 comprising a porous tubular member 102 and a longitudinal constraining member 104. Length extensible implantable device 100 can be implanted in the body of a patient either alone or in combination with one or more other components. For example, length extensible implantable device 100 can be combined with a suitable stent, forming a stent-graft. Further, length extensible implant 100 can be combined with other grafts and/or stent-grafts. In other embodiments, the length extensible graft 100 may be provided with a stent (or stent graft) on only one end or alternatively on more than one end or even each end of the length extensible graft 100. A stent graft is considered to be a stent provided with a graft covering all or a portion of the inner or outer surfaces of the stent or both the inner and outer surfaces of the stent. Devices with more than two ends are also contemplated, such as bifurcated devices. Any combination of length extensible implantable device 100 with any suitable medical device is within the scope of the present disclosure.

In various embodiments, porous tubular member 102 comprises a compressible, porous polymeric material, preferably an open celled material. For example, member 102 can comprise a porous expanded polymer, including expanded polytetrafluoroethylene ("ePTFE"), expanded modified PTFE (e.g. coated materials as described further below), expanded copolymers of PTFE, nylons, polycarbonates, polyethylenes, polypropylenes, polyurethanes and the like. These materials may also include materials having a porous fibrillated microstructure. It is also appreciated that these types of materials may be provided with coatings such as elastomeric coatings and coatings including therapeutic agents (e.g., heparin). Coatings may be provided as surface coatings or alternatively may partially or entirely impregnate the porous materials. Any suitable compressible porous polymer material is within the scope of the present disclosure.

Porous tubular member 102 can, for example, comprise an ePTFE construct. In various embodiments, porous tubular member 102 comprises a longitudinally extruded and longitudinally expanded ePTFE tube, such as the tubes described in U.S. Pat. Nos. 3,953,566 and 4,187,390. In other embodiments, polymeric tubular member 102 comprises a wrapped ePTFE film tube. For example, member 102 can comprises a tube made from an ePTFE film that has been cigarette wrapped on the surface of a mandrel or, alternatively, has been helically wrapped on the surface of a mandrel. Such ePTFE films of this type can be made generally as taught by U.S. Pat. Nos. 3,953,566 and 4,187,390. Likewise, conventional longitudinally extruded and expanded ePTFE tubes may be usefully reinforced with an external wrap of ePTFE film, typically, a helical wrap. However, any suitable porous ePTFE tubular member is within the scope of the present disclosure.

In various embodiments, porous tubular member 102 comprises an ePTFE tube having a multiplicity of fibrils which in turn can be connected to a multiplicity of nodes. The microstructure of porous tubular member 102 can comprise a multiplicity of fibrils having a mean fibril length. Mean fibril length can be determined, for example, by examining a photomicrograph of the surface of porous tubular member 102 and by taking the mean of ten measurements made in the predominant direction of the fibrils between nodes connected by fibrils. First, a photomicrograph is made of a representative region of the sample surface, of adequate magnification to show at least five sequential fibrils within the length of the photomicrograph. A series of five measurements are taken along a straight line drawn across the surface of the photomicrograph in the predominant direction of the fibrils followed by a second series of five measurements made along a second line drawn parallel to the first. A measurement constitutes the distance between adjacent nodes connected by at least one fibril. The ten measurements obtained by this method are meant to obtain the mean fibril length of the region.

Figure 2A:
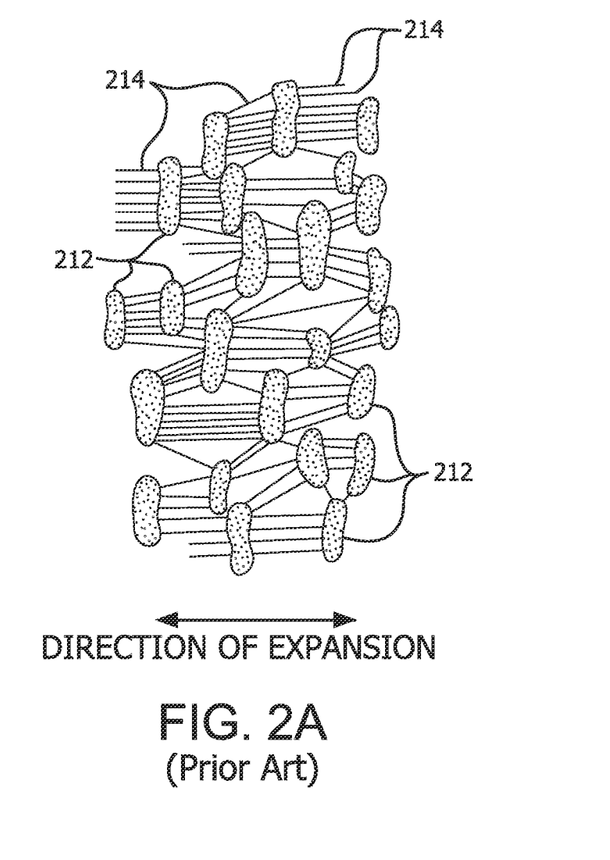
FIGS. 2A and 2B are schematic representations of a microstructure of ePTFE material of the prior art.
Figure 2B:
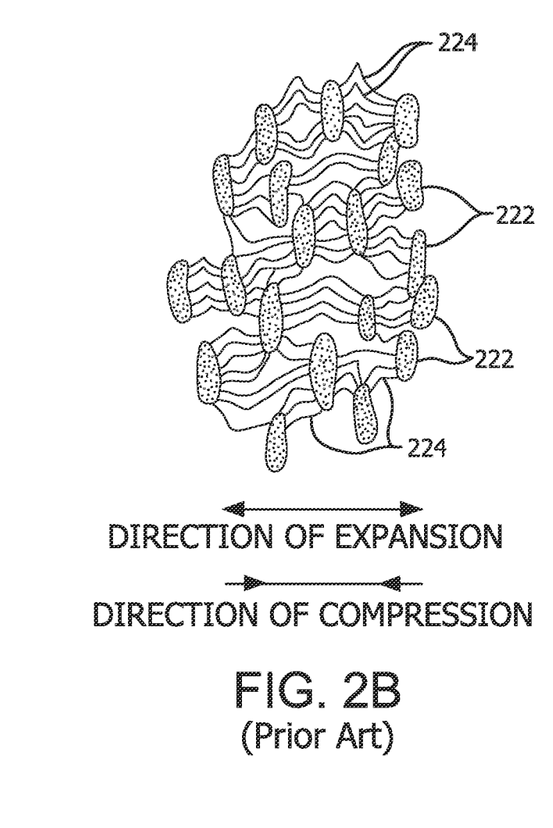

For example, as illustrated in FIGS. 2A and 2B, porous tubular member 102 can comprise a microstructure of nodes 212, 222 interconnected by fibrils 214, 224.

In various embodiments, in the longitudinally uncompressed configuration, porous tubular member 102 can comprise a multiplicity of straight or unbent fibrils 214. Similarly, visual observation of a magnified longitudinal cross section of porous tubular member 102 indicates that a majority of the fibrils straight or unbent.

For example, after longitudinal compression, portion 110 of porous tubular member 102 comprises a multiplicity of bent fibrils 224. Similarly, visual observation of a magnified longitudinal cross section of portion 110 can indicate that a majority of the fibrils 224 connected to nodes 222 are relatively straight or unbent.

In various embodiments, at least a portion of porous tubular member 102 is held in a longitudinally compressed configuration by longitudinal constraining member 104. As illustrated in FIGS. 1A-1C, in such configurations, longitudinal constraining member 104 can surround a portion 110 of an abluminal surface of porous tubular member 102 and maintain portion 110 in the longitudinally compressed configuration. In various embodiments, portion 110 is the entire length of porous tubular member 102.

In various embodiments, portion 110 of porous tubular member 102, when compressed to the laterally compressed configuration, comprises a multiplicity of bent fibrils. In such embodiments, the mean fibril length in portion 110 is shorter than the mean fibril length of porous tubular member 102 in the initial, longitudinally uncompressed configuration. Further, visual observation of a magnified surface of portion 110 can indicate that a majority of the fibrils are relatively non-parallel and bent in relation to the longitudinal axis of the tubular member.

Longitudinal constraining member 104 can be capable of rupturing when force is applied in a particular direction. For example, in configurations in which a portion 110 of porous tubular member 102 is held in the longitudinal compressed configuration, applying tension to one or both ends of porous tubular member can cause longitudinal constraining member 104 to rupture. Rupture of longitudinal constraining member 104 can permit portion 110 to extend from the longitudinally compressed configuration to a less compressed configuration having fibrils that are less bent.

In other embodiments, longitudinal constraining member 104 can be ruptured by applying a radial force. For example, a balloon can be used to apply radial force to porous tubular member 102, rupturing longitudinal constraining member 104 and permitting extension of portion 110 to a lesser compressed configuration having fibrils that are less bent.

With reference to FIGS. 1A-1C, in various embodiments, longitudinal constraining member 104 can comprise a variety of different tubular forms. For example, longitudinal constraining member 104 can comprise an ePTFE film (e.g., a porous ePTFE film). In various embodiments, longitudinal constraining member 104 comprises an a ePTFE film having a multiplicity of nodes connected by fibrils, such as those taught by U.S. Pat. Nos. 3,953,566, 4,187,390, and 5,814,405. However, any film suitable of constraining portion 110 of porous tubular member 102 in a longitudinally compressed configuration is within the scope of the present disclosure.

FIG. 1A illustrates a film wrapped around the surface of porous tubular member 102 at a low angle in relation to a longitudinal axis of the porous tubular member. For example, the film can be wrapped between about 0° and 45° relative to the longitudinal axis of porous tubular member 102.

In various embodiments, as illustrated in FIG. 1B, longitudinal constraining member 104 can comprise a film wrapped around the surface of porous tubular member 102 at a higher angle in relation to the longitudinal axis of the porous tubular member. For example, the film can be wrapped between about 45° and 90° relative to the longitudinal axis of porous tubular member 102.

In yet other embodiments, longitudinal constraining member 104 can comprise a tubular member capable of rupturing upon the application of a sufficiently large force. Such a tubular member can comprise a tubular wall having a multiplicity of slits, holes, and/or perforations that facilitate rupturing. As illustrated in FIG. 1C, longitudinal constraining member 104 can comprise, for example, a perforated tube. Although described in relation to particular examples and embodiments, any tubular member capable of maintaining porous tubular member 102 in a longitudinally compressed configuration and rupturing upon application of sufficient force is within the scope of the present disclosure.

Figure 3:
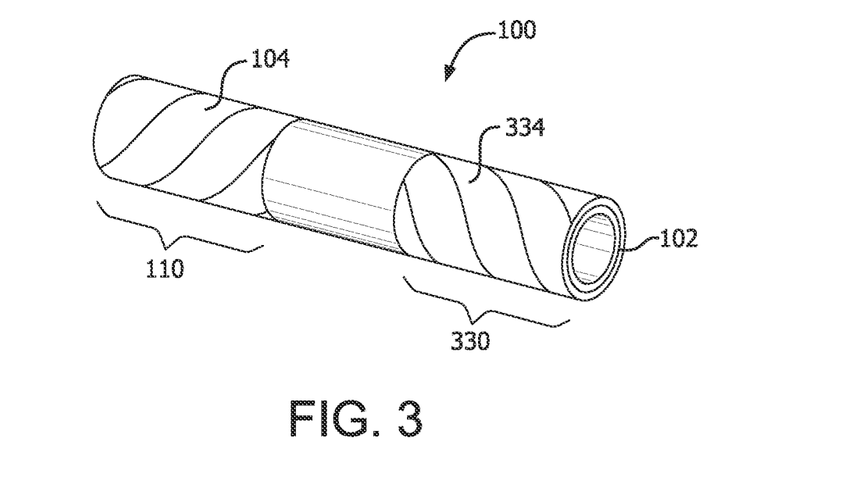
FIG. 3 is a perspective view of a length extensible implantable device in accordance with the present disclosure.

As illustrated in the perspective view of FIG. 3, implantable device 100 can comprise a first longitudinal constraining member 104 and a second longitudinal constraining member 334. For example, first longitudinal constraining member 104 can surround a first portion 110 of porous tubular member 102, and second longitudinal constraining member 334 can surround a second portion 330 of porous tubular member 102.

Figure 4:
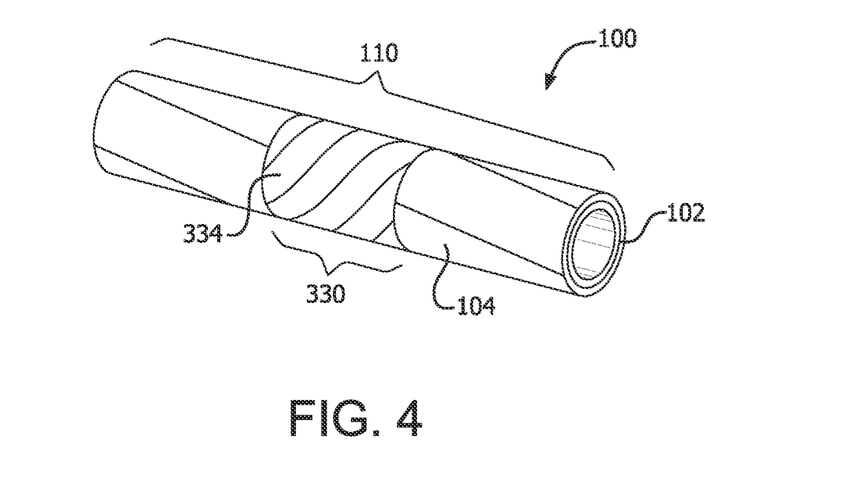
FIG. 4 is a perspective view of another length extensible implantable device in accordance with the present disclosure.

In various embodiments, first portion 110 and second portion 330 can comprise at least a part of the same portion, such that second longitudinal constraining member 334 surrounds first longitudinal constraining member 104. For example, the perspective view of FIG. 4 illustrates second longitudinal constraining member 334 surrounding second portion 330 and a part of first portion 110. Any configuration of first and second longitudinal constraining members, including partial or complete overlap of the two constraining members, is within the scope of the present disclosure. Further, the use of any number of longitudinal constraining members is within the scope of the present disclosure.

First longitudinal constraining member 104 and/or second longitudinal constraining member 334 can optionally be secured to porous tubular member 102, for example, to maintain the longitudinal constraining members in a desired orientation and position relative to porous tubular member 102. For example, first longitudinal constraining member 104 and/or second longitudinal constraining member 334 can be secured to porous tubular member 102 by applying an adhesive to a segment of an abluminal surface of porous tubular member 102 and/or the inner surface of the longitudinal constraining members. In various embodiments, a thermoplastic polymer adhesive, including a tetrafluoroethylene and perfluoromethyl vinyl ether copolymer, such as those described in U.S. Pat. No. 7,462,675, can be used. In other embodiments, a fluoroelastomer adhesive, such as a FEP, can be used. Any means capable of securing first longitudinal constraining member 104 and/or second longitudinal constraining member 334 to first porous tubular member 102 is within the scope of the present disclosure.

A method for making a length extensible implantable device of the present disclosure is described as follows. A porous tubular member in a longitudinally uncompressed configuration is obtained and fitted coaxially over a mandrel having an outside diameter the same as or slightly larger than the inside diameter of the porous tubular member. The tubular member is longitudinally compressed by a compressive force so that the length of the tube is reduced to a desired length. A longitudinal constraining member is placed over at least a portion of the porous tubular member to maintain the portion of the member in the longitudinally compressed configuration. The longitudinal constraining member can optionally be secured to the porous tubular member. The compressive force on the porous tubular member is released, and the longitudinally compressed porous tubular member is removed from the mandrel.

Figure 5A:
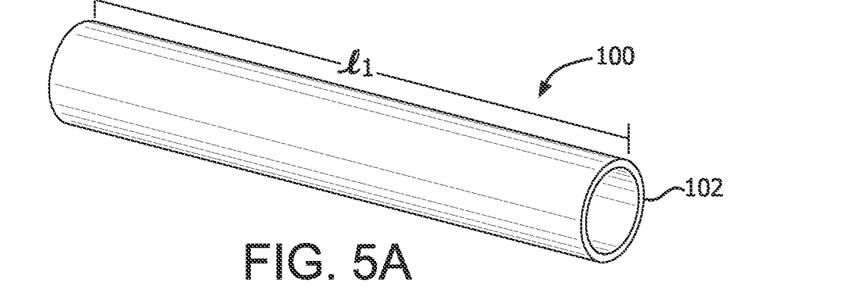
FIGS. 5A-5D are perspective views of a length extensible implantable device in various stages.

FIGS. 5A-5D illustrate a porous tubular member in various stages of a method for forming the porous tubular member into a length extensible implantable device. For example, FIG. 5A illustrates porous tubular member 102 in an initial, longitudinally uncompressed configuration. In the longitudinally uncompressed configuration, porous tubular member 102 can comprise a length $\ell 1$.

Figure 5B:
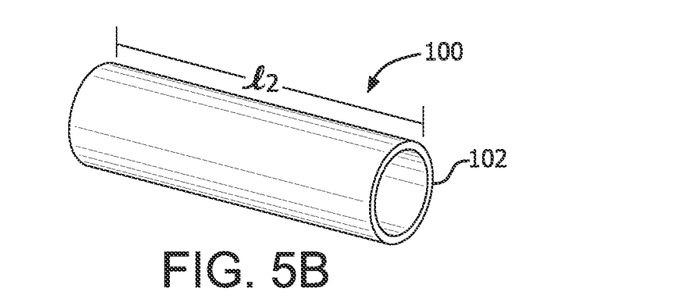

FIG. 5B illustrates porous tubular member 102 after a compressive force is applied. As the compressive force is applied, porous tubular member 102 is compressed from the initial, longitudinally uncompressed configuration to the longitudinally compressed configuration. In the longitudinally compressed configuration, porous tubular member 102 has a length $\ell 2$, which is shorter than $\ell 1$. In various embodiments, porous tubular member 102 is biased such that, upon release of the compressive force, it will at extend from $\ell 2$ at least partially back to $\ell 1$.

In various embodiments, $\ell 2$ can comprise a length that is between about 50% and 75% of $\ell 1$, such that compression from $\ell 1$ to $\ell 2$ reduces the length of porous tubular member 102 to between 50% and 75% of its uncompressed length. In other embodiments, $\ell 2$ can comprise a length that is between about 25% and 50% of $\ell 1$. In yet other embodiments, $\ell 2$ can comprise a length that is between about 5% and 25% of $\ell 1$. Any relationship between $\ell 2$ and $\ell 1$ is within the scope of the present disclosure.

Figure 5C:
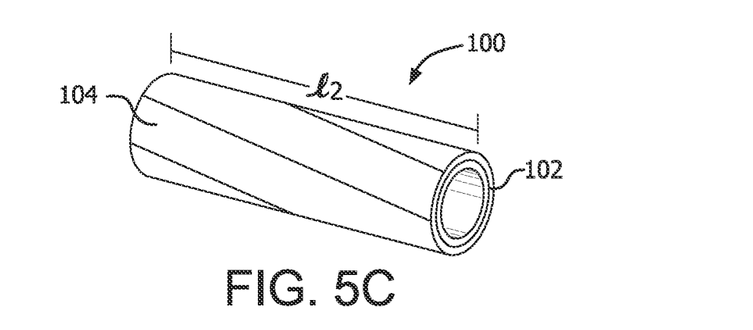

After porous tubular member 102 is compressed to a desired length $\ell 2$, at least one longitudinal constraining member 104 is applied around the abluminal surface of porous tubular member 102 to maintain at least a portion 110 of porous tubular member 102 in the longitudinally compressed configuration. For example, FIG. 5C illustrates porous tubular member 102 covered by longitudinal constraining member 104. In various embodiments, and as illustrated in FIG. 5C, portion 110 covered by longitudinal constraining member 104 can comprise the entire length ($\ell 2$) of porous tubular member 102. In other embodiments, portion 110 is less than the entire length of porous tubular members.

In various embodiments, longitudinal constraining member 104 comprises a film. In such embodiments, the film is wrapped around portion 110 of porous tubular member 102 in the longitudinally compressed configuration. As previously discussed, the film can be wrapped at a relatively low (about 0° to 45°) or a relatively high (about 45° to 90°) wrap angle relative to a longitudinal axis of porous tubular member 102. The film can also be wrapped at multiple angles, such as embodiments in which multiple layers of film are wrapped in multiple directions along the abluminal surface of porous tubular member 102.

In other embodiments, longitudinal constraining member 104 comprises a tubular element, such as a perforated tube. In such configurations, the tubular element is fitted along the surface of portion 110 of porous tubular member 102 in the longitudinally compressed configuration.

Longitudinal constraining member 104 can optionally be secured to porous tubular member 102. For example, an adhesive can be applied to the abluminal surface of porous tubular member 102. In other examples, an adhesive can be applied to the inner surface of longitudinal constraining member 104. However, as mentioned above, any manner of securing a longitudinal constraining member to a porous tubular member is within the scope of the present disclosure.

After portion 110 of porous tubular member 102 has been secured in the longitudinally compressed configuration by at least one longitudinal constraining member 104, the compressive force used to shorten porous tubular member 102 from $\ell 1$ to $\ell 2$ can be relieved while longitudinal constraining member 104 maintains portion 110 in a compressed configuration, forming length extensible implantable device 100. If portion 110 comprises less than the entire length of porous tubular member 102, upon release of the compressive force, the segment of porous tubular member 102 not constrained can expand to its original length, leaving only portion 110 in the longitudinally compressed configuration. In embodiments in which the entirety length of porous tubular member 102 is covered by longitudinal constraining member 104 (in other words, where portion 110 is equal to $\ell 2$), all of porous tubular member 102 remains in the longitudinally compressed configuration.

In various embodiments, a second porous tubular member can be positioned around portion 110, portion 330, and or all of porous tubular member 102. In such configurations, longitudinal constraining members 104 and/or 334 are sandwiched between porous tubular member 102 and a second porous tubular member, such that longitudinal constraining members 110 and/or 330 cannot be seen when visually examining the outer surface of length extensible implantable device 100.

Figure 5D:
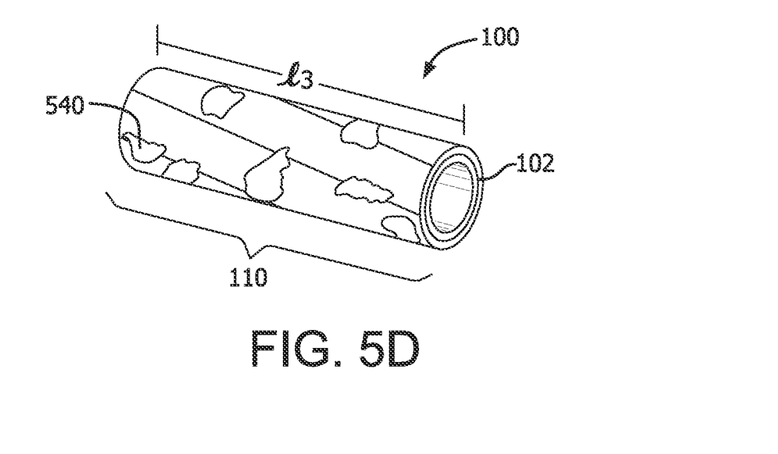

After length extensible implantable device 100 is formed, it can be adjusted and configured for use within the body of a patient. In various embodiments, as illustrated in FIG. 5D, the length of length extensible implantable device 100 can be expanded to a length $\ell 3$, which is greater than $\ell 2$ and less than or equal to the length of porous tubular member 102 in the initial, laterally uncompressed configuration (having a length of $\ell 1$). In various embodiments, as force is applied to porous tubular member 102, longitudinal constraining member 104 can rupture or tear, forming one or more ruptures 540. Once sufficient force is applied, porous tubular member 102 can continue expanding until it has expanded back to $\ell 1$.

In various embodiments, portion 110 of porous tubular member 102 can be extended from the longitudinally compressed configuration to a longer length (such as $\ell 3$) by applying a force parallel to the longitudinal axis of porous tubular member 102. In other embodiments, portion 110 of porous tubular member 102 can be extended from the longitudinally compressed configuration to $\ell 3$ by applying a radial force to portion 110.

For example, a treatment provider can determine a desired length of length extensible implantable device 100 before implanting the device into the vasculature of a patient. In other cases, the treatment provider can determine the desired length of length extensible implantable device 100 during the course of implanting the device into the vasculature and delivering the device to a treatment area of the patient.

Several characteristics and advantages have been set forth in the preceding description, including various alternatives together with details of the structure and function of the devices and methods. The disclosure is intended as illustrative only and as such is not intended to be exhaustive or limiting. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein.

What is claimed is:

1. An implantable device configured to be implanted in a body of a patient, the implantable device comprising:
    a porous member comprising a microstructure including a multiplicity of fibrils, wherein the porous member comprises a longitudinally uncompressed configuration and a longitudinally compressed configuration, wherein a mean fibril length in the longitudinally uncompressed configuration is greater than a mean fibril length in the longitudinally compressed configuration; and
    a first longitudinal constraining member covering a first portion of an abluminal surface of the porous member and configured to maintain the first portion of the abluminal surface of the porous member in the longitudinally compressed configuration for implantation in the body of the patient to repair, support, and/or replace at least a portion of a body lumen, the first longitudinal constraining member comprising a porous film.

2. The implantable device of claim 1, further comprising at least a second longitudinal constraining member.

3. The implantable device of claim 2, wherein the first and second longitudinal constraining members cover different portions of the abluminal surface of the porous member.

4. The implantable device of claim 1, wherein the first constraining member is a cylindrical perforated sleeve of porous film.

5. The implantable device of claim 4, wherein perforations of the first constraining member are configured to facilitate rupturing of the first longitudinal constraining member.

6. The implantable device of claim 4, wherein the porous film is a cylindrical perforated sleeve of porous film including at least one of slits, holes, and perforations.

7. The implantable device of claim 1, wherein the first longitudinal constraining member is configured to rupture upon application of at least one of a radial force and a longitudinal force to the implantable device.

8. The implantable device of claim 7, wherein the rupture of the first longitudinal member can permit the first portion of the abluminal surface to extend from the longitudinally compressed configuration to a less compressed configuration.

9. The implantable device of claim 8, wherein a mean fibril length in the less compressed configuration is greater than the mean fibril length in the longitudinally compressed configuration and less than the mean fibril length in the longitudinally uncompressed configuration.

10. The implantable device of claim 7, wherein the porous member has a first length in the longitudinally compressed configuration and upon application of the radial force, the porous member can be extended from the first length to a second length where the second length is longer than the first length.

11. The implantable device of claim 1, wherein the porous film is a cylindrical member.

12. The implantable device of claim 11, wherein the porous member comprises an ePTFE film.

13. The implantable device of claim 12, wherein the ePTFE film is helically wrapped.

14. An implantable device configured to be implanted in a body of a patient, the implantable device comprising:
a porous member comprising a microstructure including a multiplicity of fibrils, wherein the porous member comprises a longitudinally uncompressed configuration and a longitudinally compressed configuration, wherein a mean fibril length in the longitudinally uncompressed configuration is greater than a mean fibril length in the longitudinally compressed configuration;
a first longitudinal constraining member covering a first portion of the abluminal surface of the porous member and secured to the first portion of the abluminal surface via an adhesive, the first longitudinal constraining member configured to maintain the first portion of the abluminal surface of the porous member in the longitudinally compressed configuration at least until implantation in the body of the patient to repair, support, and/or replace at least a portion of a body lumen, the first longitudinal constraining member comprising a porous film; and
a second longitudinal constraining member covering a second portion of the abluminal surface of the porous member and secured to the second portion of the abluminal surface via an adhesive, the second longitudinal constraining member configured to maintain the second portion of the abluminal surface of the porous member in the longitudinally compressed configuration for implantation in the body of the patient,
wherein application of a longitudinal force onto the first longitudinal constraining member causes release of the first longitudinal constraining member from the first portion such that the first portion extends to the longitudinally uncompressed configuration.

15. The implantable device of claim 14, wherein application of the longitudinal force onto the second longitudinal constraining member causes release of the second longitudinal constraining member from the second portion.

16. The implantable device of claim 14, wherein the first longitudinal member is a porous film member including at least one of slits, holes, and perforations.

17. The implantable device of claim 16, wherein the first longitudinal constraining member is configured to rupture along the at least one of slits, holes, and perforations.

18. The implantable device of claim 14, wherein the second longitudinal member is a porous film member including at least one of slits, holes, and perforations.

19. An implantable device configured to be implanted in a body of a patient, the implantable device comprising:
a porous member including a microstructure including a multiplicity of fibrils, wherein the porous member comprises a longitudinally uncompressed configuration and a longitudinally compressed configuration, wherein a mean fibril length in the longitudinally uncompressed configuration is greater than a mean fibril length in the longitudinally compressed configuration; and
a first longitudinal constraining member including a cylindrical perforated sleeve, the first longitudinal constraining member covering a first portion of an abluminal surface of the porous member and configured to maintain the first portion of the abluminal surface of the porous member in the longitudinally compressed configuration for implantation in the body of the patient to repair, support, and/or replace at least a portion of a body lumen.

* * * * *